US010311748B2

(12) United States Patent
Highet et al.

(10) Patent No.: US 10,311,748 B2
(45) Date of Patent: Jun. 4, 2019

(54) INCREMENTALLY-SIZED DISHWARE SYSTEM AND METHOD OF USING SAME FOR WEIGHT MANAGEMENT

(71) Applicant: FOQUS, INC., New Smyrna Beach, FL (US)

(72) Inventors: Danuta L. Highet, New Smyrna Beach, FL (US); Roberta E. Cahn, Voorhees, NJ (US)

(73) Assignee: Foqus, Inc., New Smyrna Beach, FL (US)

( * ) Notice: Subject to any disclaimer, the term of this patent is extended or adjusted under 35 U.S.C. 154(b) by 975 days.

(21) Appl. No.: 14/056,608

(22) Filed: Oct. 17, 2013

(65) Prior Publication Data

US 2014/0045151 A1 Feb. 13, 2014

Related U.S. Application Data

(62) Division of application No. 11/888,975, filed on Aug. 3, 2007, now abandoned.

(51) Int. Cl.
*G09B 19/00* (2006.01)
*G16H 20/60* (2018.01)

(52) U.S. Cl.
CPC ......... *G09B 19/0092* (2013.01); *G16H 20/60* (2018.01)

(58) Field of Classification Search
CPC ............................ G09B 19/0092; G16H 20/60
(Continued)

(56) References Cited

U.S. PATENT DOCUMENTS

| 893,425 A | * | 7/1908 | Bell | 30/316 |
| 1,297,900 A | * | 3/1919 | Patton | 30/359 |

(Continued)

FOREIGN PATENT DOCUMENTS

| GB | 2119633 A | 11/1983 |
| WO | 2001/16921 A1 | 3/2001 |

OTHER PUBLICATIONS

"The Diet Plate®- Portion Control Made Easy", http://www.thedietplate.com, Accessed Sep. 12, 2007.

*Primary Examiner* — Melba Bumgarner
*Assistant Examiner* — Joseph B Baldori
(74) *Attorney, Agent, or Firm* — Dickinson Wright PLLC

(57) ABSTRACT

An incrementally-sized dishware system and method for weight management gradually modifies food portion consumption behavior to provide healthier eating habits. The incrementally-sized dishware system and method includes a plurality of incrementally-sized plates having successively differentiated plate surface areas. Each of the incrementally-sized plate surface areas is successively different by an increment to modify food portion delivery to a user. When utilizing the incrementally-sized dishware system and method a user selects a starting plate surface area based on a combination of weight management factors, and over time successively shifts to plates having smaller/larger plate surface areas. Interval changes between the dishes of the incrementally-sized dishware system and method adjust the amount of food consumed and rate of weight loss over time. Children using the incrementally-sized dishware system and method learn to recognize an appropriate meal size for their body size and weight, and establish healthy eating habits that carry into adulthood.

12 Claims, 4 Drawing Sheets

(58) Field of Classification Search
USPC ........................ 434/127; 73/426; D7/396.1
See application file for complete search history.

(56) References Cited

U.S. PATENT DOCUMENTS

| | | | | |
|---|---|---|---|---|
| 1,441,437 | A * | 1/1923 | Lee | 206/553 |
| 1,465,565 | A * | 8/1923 | Scheller | 530/202 |
| 1,507,968 | A * | 9/1924 | Johnson | 73/427 |
| 1,998,969 | A | 4/1935 | Schauer | |
| 2,052,510 | A * | 8/1936 | Woolverton | 425/118 |
| 2,096,825 | A * | 10/1937 | Roman | 426/114 |
| 2,188,744 | A * | 1/1940 | Turner | 40/492 |
| 2,526,602 | A | 10/1950 | Crumrine | |
| 2,613,537 | A * | 10/1952 | Di Addario | 73/426 |
| 2,799,086 | A * | 7/1957 | Tupper | 30/142 |
| 2,799,929 | A * | 7/1957 | Kurianski | 30/301 |
| 2,821,019 | A * | 1/1958 | Immink | 30/301 |
| 2,980,280 | A | 4/1961 | Herlow | |
| 3,004,340 | A * | 10/1961 | Collins | 30/316 |
| 3,030,812 | A * | 4/1962 | Lutz | 73/426 |
| D194,054 | S | 11/1962 | Grossman | |
| D200,867 | S | 4/1965 | Haifley | |
| 3,363,311 | A * | 1/1968 | Jowers | 30/113.3 |
| 3,400,591 | A * | 9/1968 | Larson | 73/426 |
| 3,498,136 | A * | 3/1970 | Le May | 73/426 |
| 3,526,138 | A * | 9/1970 | Swett et al. | 73/426 |
| 3,696,987 | A * | 10/1972 | Schuff et al. | 229/400 |
| 3,749,278 | A * | 7/1973 | von Boch-Galhau | 220/23.83 |
| 3,820,684 | A * | 6/1974 | Harrison | 206/520 |
| 3,874,085 | A * | 4/1975 | Atkins | 33/524 |
| 3,877,577 | A * | 4/1975 | Richard | 209/679 |
| 3,968,415 | A * | 7/1976 | Hafla et al. | 318/569 |
| 3,972,118 | A * | 8/1976 | Richard | 30/298.4 |
| 4,043,203 | A * | 8/1977 | Montesi | 73/427 |
| 4,075,769 | A * | 2/1978 | Young | 434/127 |
| 4,122,860 | A * | 10/1978 | Weisman | 453/8 |
| 4,137,634 | A * | 2/1979 | Klamar | 33/12 |
| 4,154,109 | A * | 5/1979 | Kelson | 73/429 |
| 4,155,502 | A * | 5/1979 | Forte | 294/146 |
| 4,165,565 | A | 8/1979 | Cloutier et al. | |
| 4,196,807 | A * | 4/1980 | Brom | 206/427 |
| 4,204,609 | A * | 5/1980 | Kuhn | 220/573.1 |
| 4,218,611 | A * | 8/1980 | Cannon | 377/20 |
| D259,460 | S * | 6/1981 | Daenen et al. | D10/46.3 |
| 4,310,316 | A | 1/1982 | Thomann | |
| D266,820 | S * | 11/1982 | Ferrin | D10/46.3 |
| 4,420,081 | A * | 12/1983 | Dart | 206/519 |
| D278,197 | S * | 4/1985 | Harper | D7/555 |
| D278,198 | S * | 4/1985 | Harper | D7/555 |
| D281,849 | S * | 12/1985 | Cantor | D7/555 |
| 4,843,716 | A * | 7/1989 | Lutzker | 30/130 |
| 4,877,119 | A | 10/1989 | Hosking | |
| 4,951,832 | A | 8/1990 | Tenney et al. | |
| 4,966,295 | A | 10/1990 | Parrish | |
| 5,007,743 | A | 4/1991 | Brennan | |
| 5,012,928 | A * | 5/1991 | Proffitt et al. | 206/508 |
| 5,048,688 | A * | 9/1991 | Hicks, Jr. | 206/501 |
| 5,065,523 | A * | 11/1991 | Chiang | 33/562 |
| D322,541 | S * | 12/1991 | Unger | D7/585 |
| 5,094,355 | A * | 3/1992 | Clark et al. | 220/4.23 |
| 5,103,563 | A * | 4/1992 | Johnson | 30/301 |
| 5,178,416 | A | 1/1993 | Wennik | |
| 5,184,745 | A * | 2/1993 | Havens et al. | 220/23.83 |
| 5,203,703 | A * | 4/1993 | Schneiderman | 434/127 |
| 5,328,051 | A * | 7/1994 | Potter et al. | 220/575 |
| D355,735 | S * | 2/1995 | Shaffer et al. | D32/53 |
| D358,074 | S * | 5/1995 | McClean | D7/672 |
| 5,419,455 | A * | 5/1995 | Russeau | 220/575 |
| D362,160 | S * | 9/1995 | Brabeck et al. | D7/645 |
| 5,454,721 | A | 10/1995 | Kuch | |
| 5,560,653 | A * | 10/1996 | Beppu | 283/117 |
| 5,586,656 | A * | 12/1996 | Abrums | 206/501 |
| 5,607,078 | A * | 3/1997 | Nordberg et al. | 220/756 |
| 5,611,440 | A * | 3/1997 | Møller | 211/70.7 |
| 5,678,716 | A * | 10/1997 | Umiker | 220/4.26 |
| 5,680,528 | A * | 10/1997 | Korszun | 345/630 |
| 5,683,251 | A * | 11/1997 | Logan et al. | 434/127 |
| D390,752 | S | 2/1998 | DeCoster | |
| D393,777 | S | 4/1998 | Bernard | |
| D394,985 | S * | 6/1998 | Curtis et al. | D7/538 |
| 5,769,229 | A | 6/1998 | Andress et al. | |
| 5,799,792 | A * | 9/1998 | Abrums | 206/508 |
| 5,833,053 | A * | 11/1998 | Wood et al. | 206/5 |
| D404,969 | S * | 2/1999 | Krenzler | D7/507 |
| 5,881,597 | A * | 3/1999 | Brooks | 73/428 |
| 5,896,990 | A * | 4/1999 | Barzana | 206/459.1 |
| D411,940 | S * | 7/1999 | Horvat | D7/507 |
| 5,938,066 | A * | 8/1999 | DeMars | 220/574.1 |
| 6,019,244 | A * | 2/2000 | Jones | 220/666 |
| D425,378 | S * | 5/2000 | Gilbertson | D7/667 |
| 6,083,006 | A * | 7/2000 | Coffman | 434/127 |
| D437,793 | S * | 2/2001 | Kaposi et al. | D10/46.2 |
| D438,125 | S * | 2/2001 | Kaposi et al. | D10/46.2 |
| D440,164 | S * | 4/2001 | Kerr | D10/46.3 |
| D443,836 | S * | 6/2001 | Wright | D10/46.3 |
| 6,296,488 | B1 | 10/2001 | Brennan et al. | |
| D450,605 | S * | 11/2001 | Wright | D10/46.3 |
| 6,311,403 | B1 * | 11/2001 | Macrini | 33/1 SD |
| 6,318,567 | B1 | 11/2001 | Braley | |
| 6,415,945 | B1 * | 7/2002 | Zank et al. | 220/657 |
| 6,457,250 | B1 * | 10/2002 | Mingus et al. | 33/562 |
| 6,488,210 | B2 * | 12/2002 | Schumi et al. | 235/488 |
| 6,491,179 | B2 * | 12/2002 | Dokun | 220/560 |
| D473,479 | S * | 4/2003 | Blair | D10/46.3 |
| D473,752 | S * | 4/2003 | Kerr | D7/505 |
| 6,585,516 | B1 | 7/2003 | Alabaster | |
| D494,012 | S * | 8/2004 | Bandy-Helderman | D7/553.6 |
| 6,796,430 | B2 * | 9/2004 | Mercier et al. | 206/505 |
| D504,045 | S * | 4/2005 | Rediske | D6/601 |
| D504,799 | S * | 5/2005 | Lawson et al. | D7/505 |
| 6,886,694 | B2 * | 5/2005 | McNeeley et al. | 206/505 |
| D512,604 | S * | 12/2005 | Panepinto | D7/505 |
| 7,044,739 | B2 | 5/2006 | Matson | |
| 7,191,524 | B2 * | 3/2007 | Longstreth | 30/151 |
| 7,201,579 | B1 * | 4/2007 | Boyum | 434/127 |
| D547,119 | S | 7/2007 | Robinson | |
| D548,115 | S * | 8/2007 | Sawhney et al. | D10/46.2 |
| 7,310,883 | B1 * | 12/2007 | Park | 33/1 C |
| D568,102 | S | 5/2008 | Ruiz de Azua | |
| 7,413,439 | B2 * | 8/2008 | Tiessen | 434/127 |
| 7,416,094 | B2 * | 8/2008 | Sokola, Sr. | 220/574 |
| D582,798 | S * | 12/2008 | Mantilla et al. | D10/46.3 |
| D584,968 | S * | 1/2009 | Mantilla et al. | D10/46.3 |
| 7,472,595 | B2 * | 1/2009 | Ploix | 73/426 |
| D586,623 | S * | 2/2009 | Dunn | D7/541 |
| D593,800 | S * | 6/2009 | Hone | D7/506 |
| 7,603,287 | B2 * | 10/2009 | Kargman | 705/15 |
| 8,684,221 | B2 * | 4/2014 | Wallace | 220/575 |
| 2002/0055087 | A1 * | 5/2002 | Hardesty | 434/127 |
| 2002/0108953 | A1 * | 8/2002 | Goralnik | 220/212 |
| 2004/0154069 | A1 * | 8/2004 | Johnson et al. | 2/106 |
| 2005/0011261 | A1 * | 1/2005 | Lyon | 73/427 |
| 2005/0014111 | A1 | 1/2005 | Matson | |
| 2006/0029698 | A1 * | 2/2006 | Watson et al. | 426/231 |
| 2006/0073441 | A1 * | 4/2006 | Kwan-Hou | 434/127 |
| 2006/0121163 | A1 * | 6/2006 | Holloway | 426/231 |
| 2006/0183086 | A1 * | 8/2006 | Brandt | 434/127 |
| 2007/0033697 | A1 * | 2/2007 | Soldwedel | 2/80 |
| 2007/0062045 | A1 * | 3/2007 | Sylvie | 30/142 |
| 2007/0131697 | A1 * | 6/2007 | Waldie | 220/503 |
| 2007/0198332 | A1 * | 8/2007 | Beny | 705/12 |
| 2007/0289973 | A1 * | 12/2007 | Acosta et al. | 220/507 |
| 2008/0076651 | A1 * | 3/2008 | Curtin et al. | 492/14 |
| 2008/0276705 | A1 * | 11/2008 | Yeung | 73/426 |
| 2009/0019709 | A1 * | 1/2009 | Fisher et al. | 30/344 |
| 2009/0084179 | A1 * | 4/2009 | Gougian | 73/427 |
| 2009/0220924 | A1 * | 9/2009 | Smith et al. | 434/127 |
| 2009/0286212 | A1 * | 11/2009 | Gordon | 434/127 |
| 2010/0015580 | A1 * | 1/2010 | Morris | 434/127 |
| 2010/0192284 | A1 * | 8/2010 | Simon | 2/236 |
| 2011/0035339 | A1 * | 2/2011 | Wilson | 705/500 |
| 2012/0077154 | A1 * | 3/2012 | Highet et al. | 434/127 |
| 2013/0047438 | A1 * | 2/2013 | Yu | 30/121.5 |

(56) References Cited

U.S. PATENT DOCUMENTS

2013/0227847 A1* 9/2013 Peake .......................... 33/17 R
2014/0255884 A1* 9/2014 Highet ......................... 434/127
2014/0281869 A1* 9/2014 Yob ............................. 715/217

* cited by examiner

INCREMENTALLY-SIZED DISHWARE SYSTEM AND METHOD OF USING SAME FOR WEIGHT MANAGEMENT

CROSS-REFERENCE TO RELATED APPLICATION

This application is a division of co-pending U.S. Non-Provisional patent application Ser. No. 11/888,975, filed Aug. 3, 2007 in the U.S. Patent and Trademark Office, the disclosure of which is incorporated herein by reference in its entirety.

BACKGROUND OF THE INVENTION

1. Field of the Invention

The present invention relates to an incrementally-sized dishware system and method for weight management; and more particularly to a dishware system wherein a plurality of incrementally-sized plates having successively decreasing plate surface areas gradually modify food portions consumed for weight management and instill healthy eating habits.

2. Description of the Prior Art

Obesity is becoming an epidemic that affects not only adults but also an increasing number of children. Many people begin a diet abruptly by immediately reducing their caloric and food intake. Oftentimes these dieters become discouraged when their appetite does not readily adjust to the caloric modifications, and they suffer from feelings of hunger and deprivation. Discomfort and discouragement replace the drive to diet. As a consequence, many would be "dieters" quit their diet altogether or go through yo-yo dieting. Family diet techniques become a necessary prerequisite for addressing weight problems that affect parents and their children when unhealthy eating habits become infused in the home. Most diet plans require a great deal of effort and "will-power" to count calories, attend meetings, choose different foods, or measure and control portion sizes.

Experts believe that losing weight slowly is healthier, and that it is important to change eating habits in order to maintain permanent weight loss. Changing eating habits includes not only modifying what an individual is eating, but also altering portion amounts through portion control. Studies show that visual perception influences food consumption. People eat more when given larger portions. Portion control adjustment over a period of time greatly facilitates healthy weight loss, as the individual's behavior towards foods and portions becomes modified. Gradual portion control presented in a discrete manner further facilitates successful dieting and healthy eating habits. With gradual portion control, those dieting (or intending to gain weight, when specific health needs so require) are not constantly reminded of their portion reduction as they are eating; this tends to relieve mental and emotional pressures that often sabotage dieting efforts. Moreover, a discrete gradual portion control device and method can be utilized when dining with guests, without making the user's diet glaringly obvious.

The vast majority of portion control and other dieting devices heretofore disclosed and utilized do not address gradual behavior modifications, and therefore are difficult to utilize over time. That is to say, those dieting devices and methods presently in vogue do not provide gradual portion control devices and discrete behavioral modifications. Instead, the majority of dieting devices and methods provide abrupt, immediate portion adjustments, which result in feelings of deprivation as the dieter's appetite does not so abruptly diminish. These portion control dieting devices generally involve plates or containers having partitioned or compartmentalized assemblies demarcated by a specific food group appointed to be utilized by a user on a daily basis.

For various examples of these compartmentalized assemblies, see the following: U.S. Pat. No. 4,877,119 to Hosking discloses a drinking-beaker assembly including a collar and volumetric structure that is appointed to serve as both a drinking vessel, especially the drinking of water in the course of a diet, and a device for determining the precise amount of liquid consumed; U.S. Pat. No. 6,296,488 to Brenkus et al. discloses a diet method and apparatus which controls the portion size by providing a plate with a plurality of compartments associated with a meal card; U.S. Design Pat. No. D194,054 to Grossman discloses an ornamental design for a plate having three compartments, wherein each of the compartments includes a picture symbol representing the food group which is to be portioned in the respective compartment; U.S. Design Pat. No. D200,867 to Haifley discloses an ornamental design for a plate or dish wherein approximately one-half of the structure includes caloric indicia thereon, which does not appear to be utilized for holding food, while the other half seems to be appointed for holding food; U.S. Design Pat. No. D281,849 to Cantor discloses an ornamental design for a diet plate that utilizes curved rib portions to apparently form food dividers or compartments to separate food items or portions; U.S. Patent Application Publication No. 2006/0029698 to Watson et al. discloses a food template adapted to be removably applied to a food bearing surface of a food holder, such as a plate to define a plurality of areas for food portions to be placed; Foreign Publication No. GB 2119633 to Mackay discloses a compartmented plate divided into different regions which are marked in a different manner, such as by color coding, to indicate the different types of foods intended to be placed in each region; and "The Diet Plate®—Portion Control Made Easy" found at www.thedietplate.com discloses a weight management system consisting of plates and cereal bowls for a family wherein the plate or cereal bowl includes markings therein to indicate the given food groups and respective portion sizes so that caloric intake is controlled.

For repositionable compartmentalized devices see: U.S. Pat. No. 4,966,295 to Parrish, which discloses a compartmentalized dieting plate having a partitioned assembly that divides the plate to form predetermined fluid capacity compartments, and in which the partition assembly may be repositioned to adjust the compartmentalized capacities as a dieters requirements change; and U.S. Pat. No. 5,007,743 to Brennan, which discloses a food metering dish including a dish member with a continuous surrounding wall defining an interior cavity having first and second concave recesses for receiving metered containers therewithin, the recesses being appointed with ribs with removable partition walls to form compartments for food portions for controlling amounts served.

These aforementioned compartmentalized plates and containers all share numerous disadvantageous stemming from abrupt changes in a person's diet. A portion conditioning dishware set is not provided. Rather, these compartmentalized dieting plates utilize dividers to form compartments for holding food to be consumed. As the portion amounts are not gradually adjusted, but are rather immediate, the user will quickly feel deprived and suffer from hunger as his or her appetite is not gradually adjusted. Behavior modification is not achieved over a gradual period of time. Moreover, these devices all create a negative emotional impact on the user, as they do not discretely provide portion control mechanism. During a dinner with friends or family it will be highly obvious that the user is on a diet or subject to portion control. Moreover, none of these devices provide the ability to gradually adjust one's food portions through implementation of a dishware set that resembles a typical plate.

Even wherein systems and methods of modifying eating habits of a user are provided, rather than just portion control, these devices fail to provide a plate set that provides incrementally-sized plates which so resemble regular plates, that a dieter (as well as others eating with the dieter) can soon forget he or she is practicing portion modification. For example, U.S. Pat. No. 7,044,739 to Matson discloses a system and method for modifying eating habits of a user by providing a set of fixed volume graduated containers that are subdivided into sections and provide a user with means to control the volume of food consumed over time. In a weight loss program, a user is provided with a set of the graduated sectioned containers and migrates from measuring the amount of food per meal with a larger fixed volume container to measuring the amount of food per meal with a smaller fixed volume container. Unfortunately, the sectioned containers cannot feasibly be utilized in a discrete manner on a dinner table during regular meals. This has particular impact when one has dinner guests, and/or when a parent is attempting to gradually, and discretely, modify eating habits of a child. Moreover, meals require constant measuring and compartmentalizing food to be consumed. The dieter is constantly burdened with the task of loading each compartment, and is constantly reminded of his or her diet during eating.

Notwithstanding the efforts of prior art workers to construct an efficient dieting device and method for modifying eating habits, there remains a need in the art for an incrementally-sized dishware system and method that provides gradual food portion reduction, so that a user can modify his/her eating habits for effective weight management without feelings of deprivation. There remains a need in the art for a dishware system that provides a plurality of incrementally-sized plates having successively decreasing plate surface areas appointed to be utilized in a graduated manner over a period of time. Additionally, there is a need in the art for a dishware set that utilizes a plurality of plates having successively decreasing plate surface areas which become decreased by way of small increments to provide subtle changes in portion amounts served, so that a user does not feel deprived and can gradually modify food portions consumed and establish healthy eating habits for effective weight management.

SUMMARY OF THE INVENTION

The present invention provides an incrementally-sized dishware system and method that provides incrementally-sized plates deployed during intervals to provide gradual food portion reduction, enabling a user to modify his/her eating habits for effective weight management without feelings of deprivation. The incrementally-sized dishware system and method provides a plurality of incrementally-sized plates having successively decreasing plate surface areas appointed to be utilized in a graduated manner over a period of time. When utilizing the incrementally-sized dishware system and method a user selects a starting plate surface area based on a combination of weight management factors, and over time successively shifts to plates having smaller/larger plate surface areas. The incrementally-sized dishware system and method utilizes a plurality of plates having successively decreasing plate surface areas that decrease by way of small increments to provide subtle changes in portion amounts served so that a user does not feel deprived and can gradually modify food portions consumed and establish healthy eating habits for effective weight management.

The incrementally-sized dishware system comprises a plurality of incrementally-sized plates forming a set. Each of the incrementally-sized plates has a plate surface area that is different from the successive or neighboring plate. Successively decreasing plate surface areas provide different food volumes/portion sizes. The plate surface areas successively decrease by an increment so that as a user shifts from each consecutive plate, the user gradually decreases (or increases, depending on weight management needs) his/her portion intake over time.

Additionally, a weight management method utilizing the incrementally-sized dishware system is provided. The first step of the method involves a user selecting a starting plate, based on the user's weight goals. The starting plate is selected from a plurality of incrementally-sized plates having successively decreasing plate surface areas. Plate surface areas of each of the incrementally-sized plates are successively differentiated by an increment in order to modify food portion intake delivered to a user. The user's selection of the starting plate is determined, based on at least one weight management factor. Next, the user utilizes the starting plate for a designated time interval in order to deliver a starting food portion amount to the user, during a meal. When a designated time interval is reached, the user adjusts his/her starting food portion amount by shifting to a successive plate selected from the incrementally-sized plates that will deliver a differentiated food portion amount to the user. Gradually, food portion amounts are adjusted as the user continuously shifts to each successive plate selected from the incrementally-sized plates each time the designated time interval is reached. Portion amounts are gradually modified until the user becomes accustomed to each portion amount and reaches the weight goal and corresponding goal portion amount. The goal portion amount is delivered by a goal plate, which is a plate selected from the incrementally-sized plates based upon at least one of the weight management factors. Through continuous use of the goal plate, i.e. the proper food serving amount for the user based on weight management factors, the user can maintain his/her ideal weight and continue to consume healthy food portions.

For illustrative purposes, the invention has been described in the specification and drawings with reference to round plates. It will be understood by those skilled in the art that the dishware can have a wide variety of shapes which are other than round. Substantially any dishware shape that permits incremental changes to be made in the surface area and volumetric capacity of the dishware, is intended to fall within the scope of the invention.

BRIEF DESCRIPTION OF THE DRAWINGS

The invention will be more fully understood and further advantages will become apparent when reference is had to the following detailed description of the preferred embodiments of the invention and the accompanying drawings, in which:

FIG. 1b illustrates a schematic view of some of the incrementally-sized plates separated from the set/stack of FIG. 1a;

DETAILED DESCRIPTION OF THE INVENTION

Figure 1A:
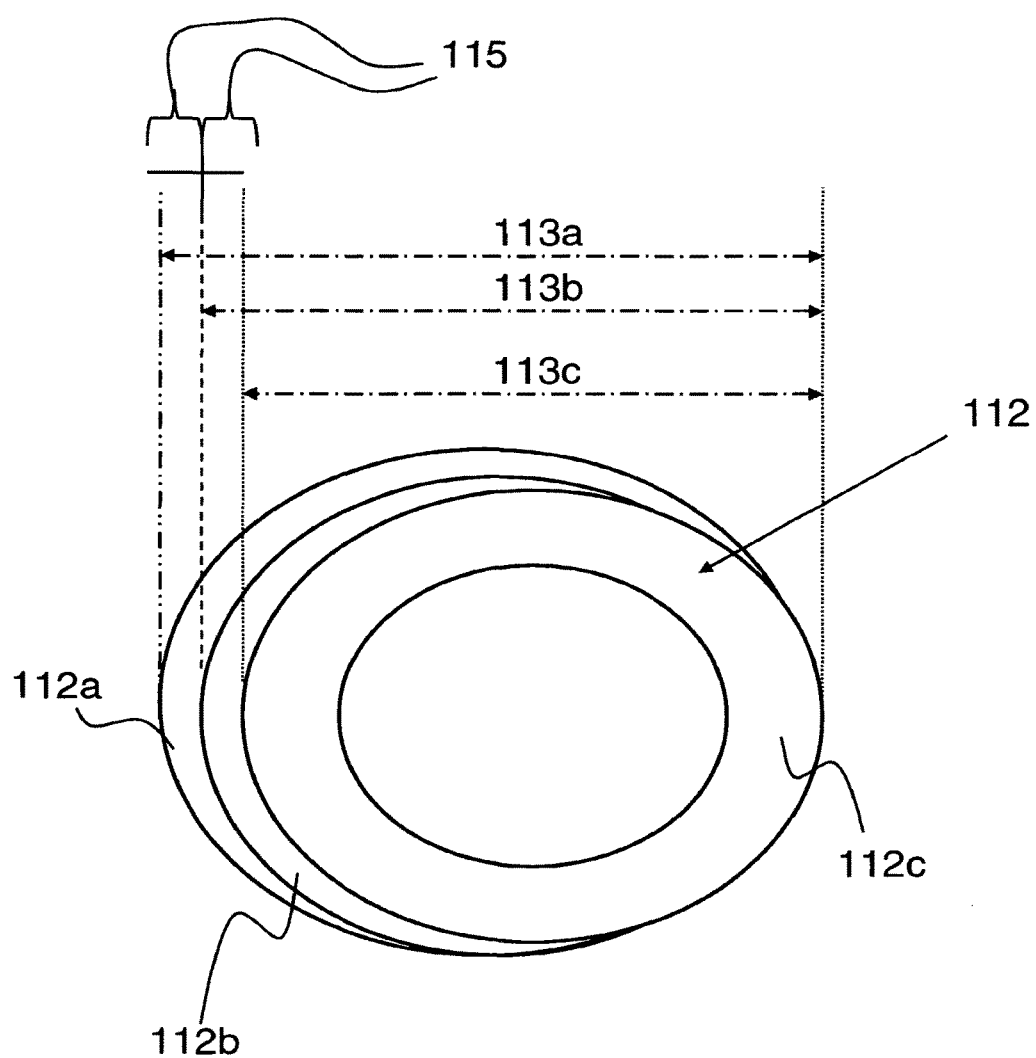
FIG. 1a illustrates a schematic view of a stack of plates of the incrementally-sized dishware system.

The incrementally-sized dishware system and method of the present invention is designed to decrease or increase serving sizes and visa vie consumption of food over a period of time, depending on a user's weight management needs. When the consumer has adjusted to the given serving size or food portion amount, the serving size is further decreased or increased, as the case may be, by utilizing the next incrementally-sized dish. Particularly, the incrementally-sized dishware system provides incrementally-sized plates appointed to be used in intervals to provide gradual food portion reduction, so that a user can modify his/her eating habits for effective weight management without feelings of deprivation. A plurality of incrementally-sized plates are provided. Each of these plates has a successively decreasing plate surface area so that each plate yields a different volume capacity for food, and hence presents a different portion amount. The plates are appointed to be utilized in a graduated manner over a period of time. Small, incremental changes in plate surface areas are successively provided, so that the food portion changes from plate to plate are subtle. Advantageously, with this arrangement, the user does not feel deprived and gradually establishes healthy eating habits for effective weight management.

Long-term use of smaller incrementally-sized plates prevents weight gain after the user's diet is complete, allowing the user to readily maintain his or her weight. This is especially useful, as dieters who are frequently successful at losing the weight frequently gain it back after a period of time. Long-term use of the plates reduces the need to track data, count calories, and calculate portion sizes, etc., after the diet. Advantageously, once a user knows their plate size, or goal plate, weight maintenance is readily achieved.

Incrementally-sized plates are provided, as well as optional place settings and utensils, to induce behavior modification, causing desired weight loss (or gain) and establishing new, healthy eating habits. Changes in dish size occur in small increments, making it difficult to notice the changes from day to day, or week to week. Small daily or weekly changes in increments utilized by the incrementally-sized dishware system and method minimize dining discomfort. The dishes are proportioned between each size so that the calorie intake is slowly reduced (or increased) and a person is dieting (or gaining weight) without significant effort and/or the recognition that a change in caloric intake is occurring. Consumers using the dishes of the incrementally-sized dishware system and method will gradually become accustomed to smaller (or larger) sized dishes and glassware, and portions of food and drink. Counting calories, measuring food portions, and dietary modifications involving departures from the user's normal foods are no longer required, owing to use of the present incrementally-sized dishware system and method.

The incrementally-sized dishware system and method has applications for use in managing an individual's weight, as well as the weight of family members, such as spouses, children and other family members. As children are beginning to have more and more weight issues, accountable in part due to eating larger portion sizes than their body build requires, weight management and healthier eating habits are needed. Children using the incrementally-sized dishware system and method will learn to recognize an appropriate meal size for their body size and weight. This learning experience enables children to establish healthy eating habits that carry on into their adult lives. The discrete nature of the incrementally-sized plates, optional bowls, cups, etc., of the system allow parents to gradually decrease a child's portion amount without the child being adversely affected, or even aware of the small, incremental decrease. A family can lose weight together. Moreover, progressive plate sizes can be used to track and accommodate growth of children. The plate sizes can be increased gradually, instead of progressing from "kiddy-sized" plates directly to adult-sized plates, which encourages overeating and may contribute to childhood obesity. In addition, schools, currently feed all children the same size portions on a single size tray or plate. School cafeterias could use different size plates to match the appropriate food portions with caloric needs of different age children.

The dishware and system could be used as part of the treatment for eating disorders such as anorexia and bulimia. For example, anorexics have a distorted view of themselves and the amount of food they consume. Starting with a small dish, they could gradually become accustomed to larger and larger dishes and portion sizes until reaching a healthy amount of food.

Figure 1B:
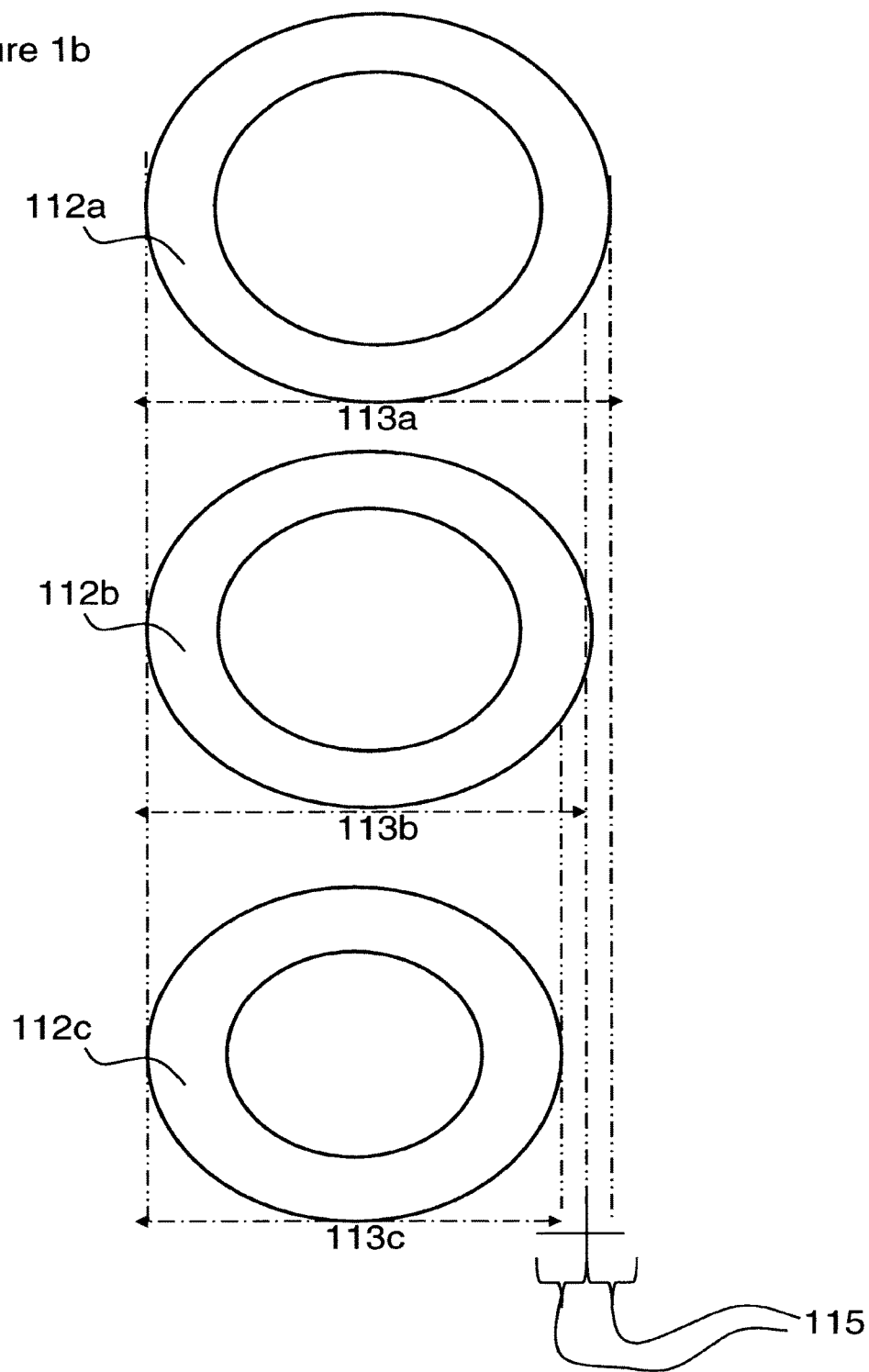

FIG. 1a illustrates a schematic view of a stack of round plates of the incrementally-sized dishware system, while FIG. 1b illustrates a schematic view of some of the round incrementally-sized plates separated from the set/stack of FIG. 1a. The incrementally-sized dishware system includes a plurality of incrementally-sized plates $112a$-$112n$ having successively decreasing plate diameters da-dn. Herein plates $112a$, $112b$ and $112c$ are shown with plate diameters da, db, dc shown herein at $113a$, $113b$ and $113c$, respectively. Plate diameters da-dn, shown at $113a$, $113b$ and $113c$, of each of the incrementally-sized plates $112a$-$112n$ are successively differentiated by an increment 115 to modify food portion intake delivered to a user. Increment 115 between successively decreasing plate diameters $112a$, $112b$ and $112c$ ranges from 1/16 inch to a 1 inch increment. Preferably, increment 115 between successively decreasing plate diameters $112a$, $112b$ and $112c$ ranges from 1/8 inch to a 1/2 inch increment. Most preferably, increment 115 between successively decreasing plate diameters $112a$, $112b$ and $112c$ is 1/4 inch. When increment 115 is small, the plate volume and visa vie diameter changes or modifications are small so that shifting to the next or successive plate goes virtually unnoticed. The smaller diameter change results in a very gradual change in plate and visa vie portion size.

The incrementally-sized dishware system and method provides a weight loss program that focuses on incremental percent rate changes by automatically adjusting the portion served to a user. For example, for a round plate, change in area is equal to the following: change in area=pi/4 ($d1^2$-$d2^2$). Even though the change in plate diameter d1-d2 is constant, the rate at which the plate surface area decreases is reduced in decreasing increments. The area of the plate is directly proportional to the volume of the plate, and therefore the total calories consumed. As an individual reduces their plate size using constant diameter changes, the amount of calories per each change in diameter is decreased. For example, when the plate is reduced from 10 to 9.75 inch diameter, the area of the plate is reduced by 3.88 square inches. Going from 5 inches to 4.75 inches, the area is reduced by 1.91 square inches, which corresponds to half the reduction of calories, assuming everything else is constant. Table I below sets forth the diameter to plate area and change in area with incremental changes of ¼ inch for each sequential round plate. It also shows how the standardized plate size corresponds to round and square plate areas. The standardized plate size dimensions assume a flat plate.

TABLE I

| Standard Size | Surface Area Range (in$^2$) | Square Plate Width (in) | Square Plate Area (in$^2$) | Round Plate Diameter (inches) | Round Plate Area (in$^2$) | Round Plate Change in Area (in$^2$) |
|---|---|---|---|---|---|---|
| 24 | 78-81 | 9 | 81.00 | 10 | 78.54 | |
| 23 | 72-76 | 8.75 | 76.56 | 9.75 | 74.66 | 3.88 |
| 22 | 68-72 | 8.5 | 72.25 | 9.5 | 70.88 | 3.78 |
| 21 | 64-68 | 8.25 | 68.06 | 9.25 | 67.20 | 3.68 |
| 20 | 61-64 | 8 | 64.00 | 9 | 63.62 | 3.58 |
| 19 | 58-61 | 7.75 | 60.06 | 8.75 | 60.13 | 3.49 |
| 18 | 55-58 | 7.5 | 56.25 | 8.5 | 56.74 | 3.39 |
| 17 | 52-55 | 7.25 | 52.56 | 8.25 | 53.46 | 3.29 |
| 16 | 49-52 | 7 | 49.00 | 8 | 50.27 | 3.19 |
| 15 | 46-49 | 6.75 | 45.56 | 7.75 | 47.17 | 3.09 |
| 14 | 43-46 | 6.5 | 42.25 | 7.5 | 44.18 | 2.99 |
| 13 | 40-43 | 6.375 | 40.64 | 7.25 | 41.28 | 2.90 |
| 12 | 37-40 | 6.25 | 39.06 | 7 | 38.48 | 2.80 |
| 11 | 34-37 | 6 | 36.00 | 6.75 | 35.78 | 2.70 |
| 10 | 31-34 | 5.75 | 33.06 | 6.5 | 33.18 | 2.60 |
| 9 | 29-31 | 5.5 | 30.25 | 6.25 | 30.68 | 2.50 |
| 8 | 27-29 | 5.25 | 27.56 | 6 | 28.27 | 2.41 |
| 7 | 25-27 | 5 | 25.00 | 5.75 | 25.97 | 2.31 |
| 6 | 23-25 | 4.75 | 22.56 | 5.5 | 23.76 | 2.21 |
| 5 | 21-23 | 4.5 | 20.25 | 5.25 | 21.65 | 2.11 |
| 4 | 19-21 | 4.25 | 18.06 | 5 | 19.63 | 2.01 |
| 3 | 17-19 | 4.125 | 17.02 | 4.75 | 17.72 | 1.91 |
| 2 | 15-17 | 4 | 16.00 | 4.5 | 15.90 | 1.82 |
| 1 | 13-15 | 3.75 | 14.06 | 4.25 | 14.19 | 1.72 |
| 0 | 11-13 | 3.5 | 12.25 | 4 | 12.57 | 1.62 |

For example: Family of four starting a weight loss initiative together using round plates: Father 300 lbs (plate size 10"), mother 200 lbs (plate size 8.5"), child 1 170 lbs (plate size 8"), and child 2 150 lbs (plate size 7.5"). They all start with plate sizes they feel comfortable with; when they go to the sequential plate size, their plates each reduce area by different amounts. Father goes down by 3.88 sq. in., mother by 3.29 sq. in., child 1 by 3.09 sq. in., and child 2 by 2.90 sq. in. They can motivate each other by reducing the plates by one size, but the calorie reduction will be different for each person. Obesity tends to run in families. The plate size variety can help parents realize that children need a plate size that corresponds to their size.

A plurality of plates is provided to form a set of incrementally-sized plates. Specifically, if using round plates, wherein the smallest plates has a diameter of 4 inches and a last plate has a largest plate diameter of 10 inches, and the plates are consecutively decreased by an increment of ¼ inch, twenty-five incrementally-sized plates are provided, as in the example hereinabove (see Table I). Preferably, the smallest plate has a diameter of 7 inches. This represents the smallest plate in the main or dinner plate set for most purposes. As discussed hereinafter, smaller plates can, optionally, be used as dinner plates for people that require a greater calorie restriction. The user shifts from using a starting plate selected from the incrementally-sized plates 112a-112n to the next, successive plate size at a designated time interval to correspondingly modify said food portion intake. The user continues to successively shift from plates within the incrementally-sized plates 112a-112n until the user reaches a goal food portion or weight. The person using the plates 112a-112n would start with a dinner plate size closest to their current plate size (i.e. the starting plate) and decrease one plate size at each designated time interval, such as every few days, or once per week, or longer if necessary. Generally, the time interval ranges from every two days to every month, and preferably is one week. With each new time interval, the user shifts to the next successive plate. Preferably, a chart designating the plate appointed for selection from the incrementally-sized plates 112a-112n is provided for determining a user's starting plate size as well as their end-use/goal plate size. The goal plate size is especially well suited for long term use in order to maintain a desired weight. Various weight management factors are utilized to determine the starting plate and goal plate, as well as the rate of shifting between successive plates. These factors preferably include, in combination, height, weight, gender, and activity level. To gain or loose weight, a person would have to move beyond their goal plate size; how much beyond depends in part on how quickly they want to gain or loose weight. A chart of goal plate vs. clothing sized (based on a typical height-weight range) can also be provided to help dieters meet their goal. The time interval for shifting between plates, and whether a user shifts consecutively or skips plates, is partially determined by the rate of weight loss the user is seeking. If the user is seeking rapid weight loss, the user may utilize a shorter time interval between plates, and/or may even skip plates to use smaller surface area plates on a more accelerated level, thereby facilitating cut-back on food portion amounts on a more accelerated level. The system may further comprise a plurality of incrementally-sized minor plates designed to be used for lunch, dessert, salads, appetizers, or bread. Preferably, if using round plates, the smallest plate sized plate diameter of the incrementally-sized minor plates is at least 4 inches, while the largest plate diameter of the minor plates is at least 7 inches, with successive plate sizes decreasing via ¼ inch diameter increments. These optional incrementally-sized minor plates also have significance for serving children and/or adults who need a larger reduction/increase in weight.

Figure 2:
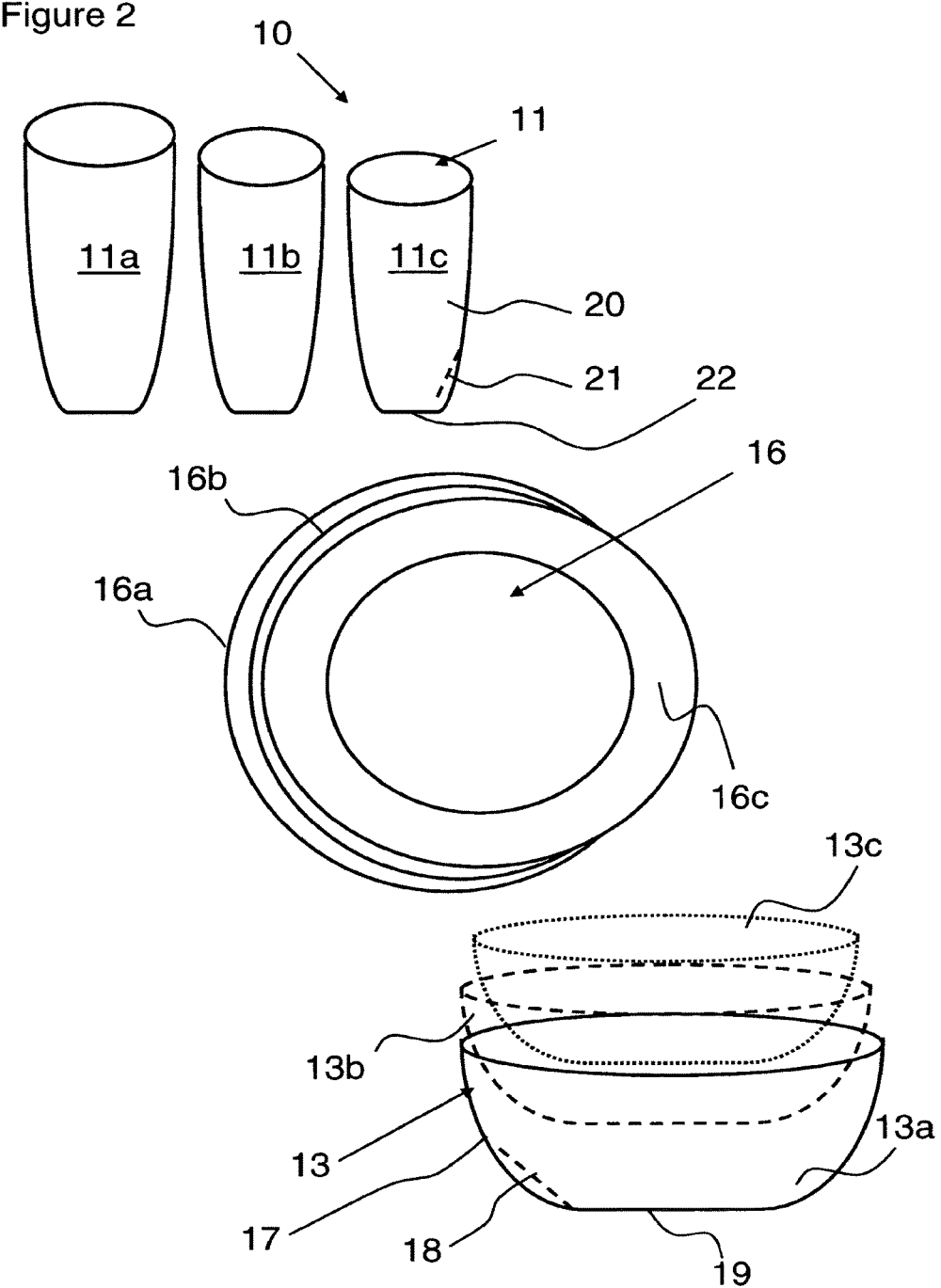
FIG. 2 illustrates a schematic view of an embodiment of the incrementally-sized dishware system wherein the set further includes optional incrementally-sized glasses and bowls.

FIG. 2 illustrates schematically an embodiment of the incrementally-sized dishware system wherein a set of plates optionally includes incrementally-sized glasses and bowls, shown generally at 10. The incrementally-sized dishware system may further comprise a plurality of incrementally-sized bowls 13a-13n, salad plates 16a-16n and/desert plates corresponding to each of the plurality of plates of FIG. 1, to form a plurality of incrementally-sized place settings a-n, as well as an optional plurality of incrementally-sized beverage containers 11a-11n. Incrementally-sized bowls 13a-13n comprise side walls 17 having a slope 18 and being oriented in relation to a bowl bottom 19 to form a bowl width. Each of bowls 13a-13n has a volume that incrementally differs by slightly adjusting slope 18, the height of side walls 17, and/or bowl bottom 19. Bowls 13a-13n could start at 7 inches and decrease in size to 4 inches. The bowls 13a-13n may include changing overall shape of the bowl and shapes and slopes of the sides in addition to the overall width in order to help reduce volume and decrease consumption while maintaining visually the perception that a larger quantity of food is contained within the bowl.

Incrementally-sized beverage containers 11a-11n are preferably selected from a group consisting of glasses, cups, or mugs. Beverage containers 11a-11n may successively decrease in height or/and in width to reduce volume by one fluid ounce for each of the beverage containers 11a-11n.

Each beverage container 11a-11n comprises a vessel having sides 20 arranged with a slope 21 in relation to a bottom 22, so that sides 20, slope 21, and/or bottom 22 may be incrementally reduced to create a volume capacity reduction of one fluid ounce for each successive size change. Beverage glassware (glasses, cups, mugs, etc.) 11a-11n could decrease in both height and width to reduce volume by one fluid ounce per size change. The shape and slope of the sides of the glassware 11a-11n can also be varied to control the volume of liquid, while minimizing the visual impact of the reduction.

Like plates 12a-12n of FIGS. 1a, 1b, the place setting's bowls 13a-13n, salad plates 16a-16n and/desert plates, and glasses 11a-11n are provided so that each member, bowl or glass, has different incremental sizes, 13a, 13b, 13c, 16a-16n and 11a, 11b, 11c, respectively, and delivers varying portion amounts. Through use of a place setting, a user can set his or her table as usual, and when having dinner guests, the user will discretely continue on with his/her dieting goals.

Figure 3A:
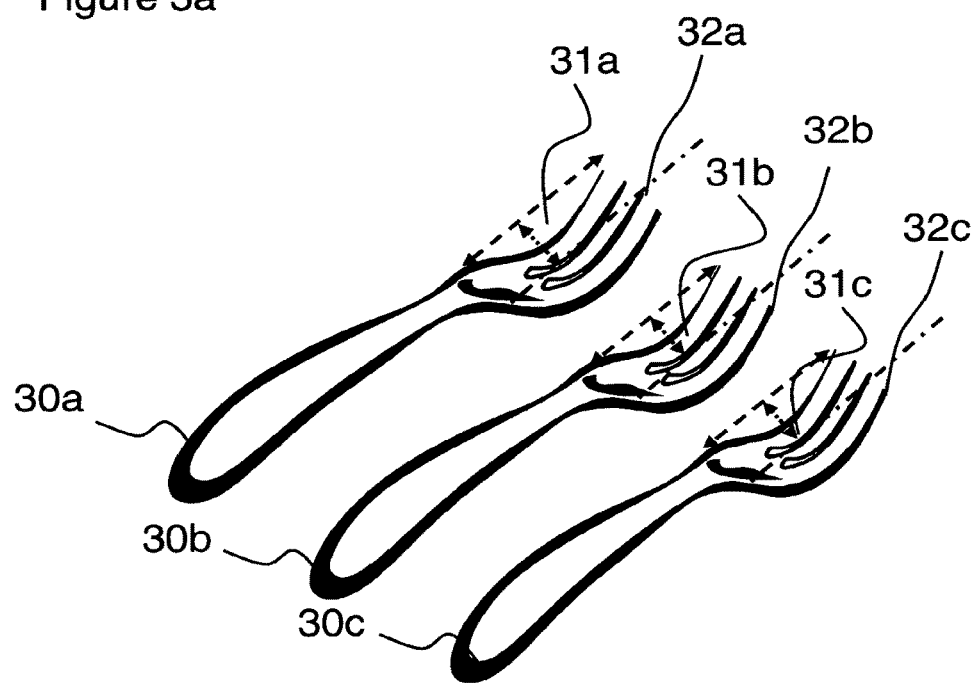
FIG. 3a illustrates a schematic view of optional incrementally-sized forks.
Figure 3B:
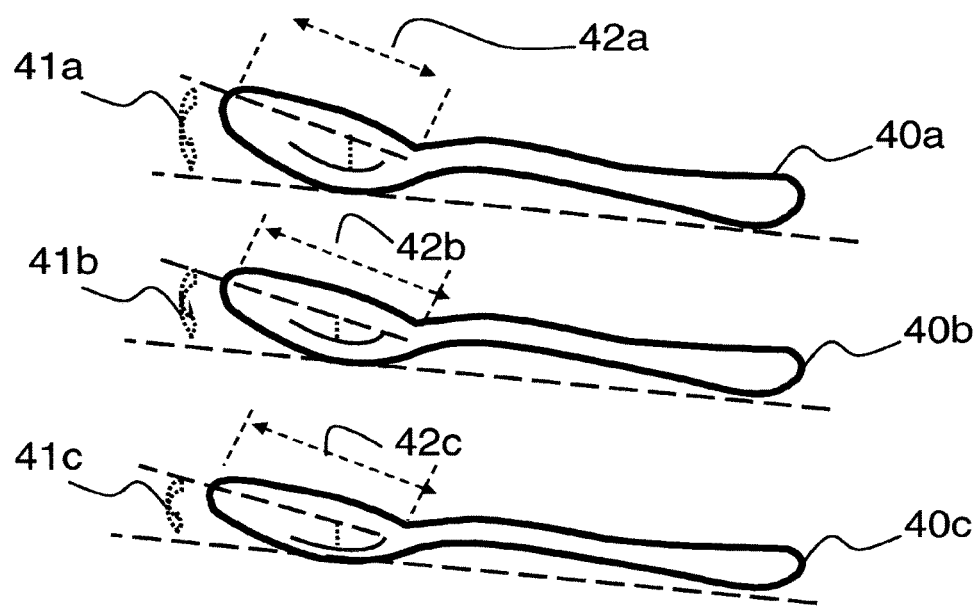
FIG. 3b illustrates a schematic view of optional incrementally-sized tea spoons.

FIGS. 3a and 3b illustrate schematic views of optional incrementally-sized utensils, including incrementally-sized forks and incrementally-sized spoons. A plurality of incrementally-sized forks 30a-30n and/spoons 40a-40n may be provided for delivering incrementally successively smaller bite sizes to the user. As a result, the user will be forced to eat more slowly as each bite is decreased in volume from the user's normal bite size. Forks 30a-30n may deliver smaller bites based on incrementally reducing each forks depth 31a-31n or by shortening prongs 32a-32n. In turn, spoons 40a-40n may deliver smaller spoonfuls based on incrementally reducing each spoons depth 41a-41n or by shortening scoop length 42a-42n.

Each of the plates, optional bowls, minor plates, salad/dessert plates, cups, mugs, and glasses may include encouraging reinforcement indicia to motivate the user to continue on with their weight management plan and to shift to the next successive plate, bowl, etc. To account for differences in plate capacity due to different shapes and dimensions, standardized plate sizes based on volumetric capacity ranges can be established and imprinted on the back of each plate for easy user identification. Moreover, a restaurant plate system may be provided wherein a plurality of incrementally-sized restaurant plates are presented with portion amounts that can be readily compared to the incrementally-sized plates used in a user's home. With this arrangement, the user can maintain his or her portion modification in a restaurant environment. A system of standardized or relative plate sizes could be utilized in restaurants and other eateries so that people can compare restaurant plates and portions with their own goals, or with normally-used plate sizes. The ratio of the diameters, the ratio of surface areas, or a ratio of the estimated volumes of the restaurant plate to the standard plate can be provided to diners. In addition, that ratio, or other suitable indicia such as standardized plate size, plate diameter, surface area, volumetric capacity, or the like, can be designated on the bottom of each plate, to facilitate distribution of plate settings among family members having divergent plate size requirements.

The incrementally-sized dishware can be produced as permanent dishes, composed of glass, ceramic, plastic, or the like. Alternatively, the incrementally-sized dishware can be produced as a disposable product, composed of paper, Styrofoam, plastic, or the like. Different colors of dishware could be available. Research has shown that color influences appetite and food intake. Different color plates can be used to increase appetite for those who want to gain weight, and decrease appetite for those who want to loose weight. Plates can be indistinguishable so that a parent can modify food intake without the awareness of the family members.

Advantageously, the incrementally-sized dishware system and method provides plates and/or dish sets designed to decrease or increase consumption of food or drink over time with minimal impact on the consumer. Visual perceptions and habits greatly influence the quantity of food/liquid consumed. Dishes comprise part of a set; the size of the dishes change from set to set. Dish size changes occur in small increments, making it difficult to notice the changes from day to day, or week to week. Small daily or weekly changes in increments utilized by the incrementally-sized dishware system and method minimize the discomfort and feelings of deprivation that many people experience when dieting. The dishes are proportioned between each size so that the calorie intake is slowly reduced (or increased) and a person diets (or gains weight) without significant effort and/or the recognition that a change in caloric intake is occurring. Consumers using the dishes of the incrementally-sized dishware system and method will gradually become accustomed to smaller (or larger) sized dishes and glassware, and portions of food and drink. Counting calories and measuring out food portions is no longer necessary, nor are dietary modifications involving departures from the user's normal foods. Advantageously, the user simply adjusts his/her portion size at an individualized pace by shifting to the next plate size.

Having thus described the invention in rather full detail, it will be understood that such detail need not be strictly adhered to. For example, the dish geometry can be circular, oval, polygonal or the like. Substantially any dishware geometry that permits incremental changes to be made in the surface area and volumetric capacity of the dishware, is intended to fall within the scope of the invention. Additional changes and modifications may suggest themselves to one skilled in the art, for example, the invention is suitable for use with plates, bowls and drinkware having a round, oval, square, cylindrical, cubic or polygonal configuration. These and other modifications which become apparent to those skilled in the art are intended to fall within the scope of the invention as defined by the subjoined claims.

What is claimed is:

1. A method, comprising:
   selecting a plate with a surface area within a range of 11-13 in$^2$ and designating the selected plate as a zero on a whole-number numerical index;
   selecting a plate increment between $\frac{1}{16}$-inch and 1 inch;
   designating a whole number (N) in the index to correspond with a plate having a first dimension equal to a first dimension of a corresponding plate (N−1) plus the plate increment
   providing a series of different-sized plates, each successive-sized plate's first dimension differing from its series neighbor by the plate increment; and
   marking the index value corresponding to the respective plates on each of the series of different-sized plates;
   selecting a utensil increment, the increment being one of a utensil length increment or a utensil depth increment;
   providing a series of different-sized eating utensils, each successive-sized utensil differing from its series neighbor by the utensil increment;
   assigning a smallest utensil in the series of different-sized eating utensils a value of zero;
   marking the smallest utensil with a zero;
   marking each successively larger utensil with a successive number of the same index that the plates are marked with.

2. The method according to claim 1, further comprising:
calculating a volume of each plate based on the plate's surface area and a 1 inch height;
correlating each plate volume with its corresponding index entry;
correlating each entry on the index to a volume for another type of dishware that is different from a plate; and
marking each dishware in a plurality of incrementally-sized dishware to match the respective dishware volumes with the corresponding index entry.

3. The method according to claim 2, wherein the dishware is at least one of bowls, templates, place settings, or beverage containers.

4. The method according to claim 2, further comprising systematically employing the incrementally-sized dishware to adjust meal size.

5. The method according to claim 1, wherein each of the series of different-sized plates is flat.

6. The method according to claim 1, wherein:
each of the series of different-sized eating utensils is one of a fork and spoon the plurality of incrementally-sized utensils provides incremental bite sizes.

7. The method according to claim 1, wherein the numerical index begins at zero.

8. The method according to claim 1, further comprising marking each of the plurality of different-sized plates with encouraging reinforcement indicia for motivating a user to shift to a successive sized plate.

9. The method according to claim 1, further comprising systematically employing the plurality of different-sized plates and the table to adjust meal size.

10. The method according to claim 1, further comprising selecting the plate increment to minimize a visual difference between consecutively-sized plates.

11. The method according to claim 1, wherein each of the series of different-sized plates is non-flat.

12. The method according to claim 1, further comprising:
assigning a relationship between clothing size and the whole number numerical index; and
embodying the relationship between the whole-number numerical index and clothing size in a table.

* * * * *